United States Patent [19]

Frank et al.

[11] Patent Number: 4,587,228
[45] Date of Patent: * May 6, 1986

[54] MOLDED IRON CATALYST MATERIAL AND ITS PREPARATION

[75] Inventors: Gerhard Frank, Hirschberg; Gerald Neubauer, Weinheim, both of Fed. Rep. of Germany

[73] Assignee: BASF Aktiengesellschaft, Fed. Rep. of Germany

[*] Notice: The portion of the term of this patent subsequent to Jun. 4, 2002 has been disclaimed.

[21] Appl. No.: 694,778

[22] Filed: Jan. 25, 1985

[30] Foreign Application Priority Data

Jan. 27, 1984 [DE] Fed. Rep. of Germany ....... 3402734

[51] Int. Cl.$^4$ .......................... B01J 23/74; B01J 27/20
[52] U.S. Cl. .................................... 502/185; 502/338; 564/492
[58] Field of Search ................. 502/185, 338; 564/492

[56] References Cited

U.S. PATENT DOCUMENTS

| | | | |
|---|---|---|---|
| 3,082,067 | 3/1963 | Hund et al. | 23/200 |
| 3,232,888 | 2/1966 | Adam et al. | 252/435 |
| 3,986,985 | 10/1976 | Dewdney et al. | 252/472 |
| 4,064,172 | 12/1977 | Gordon et al. | 260/583 |
| 4,480,051 | 10/1984 | Wu | 564/492 X |

FOREIGN PATENT DOCUMENTS 1143390 2/1969 United Kingdom .

*Primary Examiner*—W. J. Shine
*Attorney, Agent, or Firm*—Keil & Weinkauf

[57] ABSTRACT

A molded iron catalyst material which has an indentation hardness of from 850 to 1500 kp/cm$^2$ and contains metallic iron particles, obtained from iron oxide particles by contact with hydrogen at less than 500° C., and a lubricant, its preparation and its use.

8 Claims, No Drawings

MOLDED IRON CATALYST MATERIAL AND ITS PREPARATION

The present invention relates to a molded iron catalyst material containing metallic iron particles and a lubricant, and its preparation and use.

In the preparation of amines by hydrogenation of nitriles, for example hexamethylenediamine from adiponitrile, cobalt-containing catalysts are preferably used because of their high selectivity. Such processes are disclosed in, for example, German Pat. No. 1,072,972 and 1,259,899. However, the life of the cobalt catalysts used no longer meets the technical requirements, and it has in fact been found that such cobalt catalysts decompose increasingly during use. Moreover, findings indicate that dusts of metallic cobalt and its springly soluble compounds should be avoided for reasons relating to industrial hygiene.

Iron-containing catalysts have also been used for the hydrogenation of nitriles to amines. However, when iron catalysts are used, higher temperatures have to be employed. This leads to the formation of a greater amount of by-products, such as azacycloheptane, and diamines, such as 2-aminomethylcyclopentylamine and 1,2-diaminocyclohexane, which are difficult to separate off from the hexamethylenediamine, and to the formation of bis-hexamethylenetriamine and oligomers. Germain Laid-Open Application DOS No. 2,429,293 discloses that melting magnetite and carrying out reduction with hydrogen gives a catalyst which achieves a selectivity of from 98 to 99% with respect to hexamethylenediamine, at hot spot temperatures of from 150° to 170° C. However, the content of 1,2-diaminocyclohexane is 0.2% by weight. Hence, the conventional catalysts are unsatisfactory.

It is an object of the present invention to provide catalysts which have a long life in the hydrogenation of nitriles to amines and do not tend to decompose, and furthermore permit relatively low hydrogenation temperatures, produce a small amount of by-products and have a high selectivity.

We have found that this object is achieved by molded iron catalyst materials which contain metallic iron particles, obtained from iron oxide particles by contact with hydrogen at $\leq 500°$ C., and a lubricant, and have an indentation hardness of from 850 to 1500 kp/cm$^2$.

The present invention furthermore relates to a process for the preparation of molded iron catalyst materials containing metallic iron particles and a lubricant, by
(a) reduction of iron oxide particles with hydrogen at from 250° to 500° C. to give metallic iron particles,
(b) passivation of the iron particles by treatment with an inert gas containing molecular oxygen,
(c) pressing of the passivated iron particles with a lubricant to give moldings, and
(d) activation of the moldings by treatment with hydrogen at from 250° to 500° C.,
wherein the activated molded iron catalyst material is passivated by treatment with an inert gas containing molecular oxygen, and activated by subsequent treatment with hydrogen at from 250° to 500° C., these steps being carried out once or several times.

The present invention furthermore relates to the use of the molded iron catalyst materials for the hydrogenation of organic nitriles to the corresponding amines.

The novel iron catalyst materials have the advantages of a long life and, because of their hardness, of superior mechanical properties even after prolonged use. Another advantage of the novel catalysts is that they have a high selectivity at fairly low temperatures. Moreover, they give a smaller amount of by-products which are difficult to separate off from the desired products.

The novel catalyst material contains metallic iron particles which are obtained from iron oxide particles having a mean particle size of, preferably, from 0.1 to 2 μm, in particular from 0.2 to 1.2 μm, by contact with hydrogen at $\leq 500°$ C. Preferably, the metallic iron particles have a degree of reduction greater than 95%. The degree of reduction is the amount, in percent, of available iron present in metallic form.

Anisometric, eg. acicular, gamma-iron oxides, in particular gamma-iron(III) oxide and gamma-iron(III) oxide hydroxide, are preferably used. Gamma-iron(III) oxide hydroxide, which is known under the same lepidocrocite, is particularly preferably used, and is obtainable by, for example, the method described in German Published Application DAS No. 1,061,760. As a rule, the anisometric iron oxides have a particle length of from 0.1 to 2 μm, a length-to-width ratio of from 5:1 to 40:1 and a BET specific surface area of from 25 to 80 m$^2$. The heated products of the stated iron(III) oxides can also be used, heating advantageously being effected at from 250° to 700° C. Advantageously, the iron oxides used have an alkali metal content of less than 0.1% by weight, calculated as Na$_2$O.

The iron catalyst material according to the invention furthermore contains a lubricant, for example an inorganic substance having a framework structure, such as talc or graphite. The catalysts advantageously contain a lubricant in an amount of from 1 to 5% by weight, based on the total catalyst material consisting of iron particles and lubricant. Graphite has proven a particularly useful lubricant. The novel catalyst material therefore essentially consists of metallic iron particles, small amounts of iron oxide corresponding to the degree of reduction, and a lubricant.

The novel iron catalyst material is molded, for example in the form of spheres, tablets or extrudates, and has an indentation hardness of from 850 to 1500, in particular from 900 to 1300, kp/cm$^2$.

The catalyst materials according to the invention are advantageously prepared using iron oxide particles, eg. a gamma-iron(III) oxide, in particular gamma-iron(III) oxide hydroxide (lepidocrocite). It is also possible to use the heated products of the stated iron(III) oxides, heating advantageously being effected at from 250° to 700° C. Gamma-iron(III) oxide hydroxide is obtained, for example, from an aqueous solution of an iron salt with sodium hydroxide solution by a method as described in German Published Application DAS No. 1,061,760. Advantageously, the gamma-iron oxide hydroxide particles are washed until the alkali metal content is less than 0.1% by weight, calculated as Na$_2$O.

The acicular iron(III) oxide particles are reduced with hydrogen, for example in a fluidized bed in a rotary tube furnace or, preferably, in an agitated fixed bed at from 260° to 500° C., in particular from 300° to 450° C., for example in the course of from 3 to 36 hours. Advantageously, a stream of dry hydrogen is used, a relatively high hydrogen flow rate being maintained. It has proved useful to use not less than a 60-fold excess of hydrogen. The reduction is preferably carried out until the degree of reduction is greater than 95%. Metal particles obtained in this manner and essentially consisting of iron still possess substantially the form of the starting materials, and are homogeneous in spite of the preceding transformation reaction.

The metallic iron particles are then passivated. In this procedure, the metal particles are enveloped in an oxide layer by controlled oxidation, in order to eliminate the pyrophoricity due to the large free surface area of the small particles. This is achieved by passing an inert gas containing molecular oxygen, eg. an air/nitrogen mixture, over the metal powder while exactly maintaining a temperature which preferably does not exceed 100° C., in particular 80° C. After the stabilization, the degree of reduction is advantageously no lower than 80%, preferably no lower than 90%. The stabilized iron particles have, as a rule, a BET specific surface area of from 4 to 25, preferably from 8 to 12, $m^2/g$ and a particle length of from 0.05 to 2 μm.

The iron particles passivated in this manner are mixed with an inert lubricant, preferably graphite, the amount of lubricant advantageously being from 2 to 5% by weight, based on the sum of the iron particles and the lubricant. The mixture of the passivated iron particles and the lubricant is processed to moldings, eg. tablets, advantageously under a nitrogen atmosphere. The indentation hardness of the moldings should be about 300 $kp/cm^2$.

The moldings obtained in this manner are activated by treatment with a relatively large excess of hydrogen at from 250° to 500° C., in particular from 300° to 360° C., under atmospheric or superatmospheric pressure, eg. from 100 150 bar. In this procedure, the degree of reduction reached should advantageously be greater than 95%. The activation procedure increases the indentation hardness of the moldings, for example from 300 to 600-800 $kp/cm^2$.

An essential feature of the invention is that the resulting activated, molded iron catalyst materials (moldings) are passivated by treatment with an inert gas containing molecular oxygen, and activated by subsequent treatment with hydrogen at from 250° to 500° C., these steps being carried out once or several times. The conditions for the passivation and activation correspond to those mentioned above. This passivation and activation is advantageously repeated from once to 5, eg. from 2 to 4, times. The indentation hardness of the moldings increases with each activation process, and reaches a value of from 850 to 1500, in particular from 900 to 1300, $kp/cm^2$.

The novel molded iron catalysts have a high activity, which permits the reaction to be carried out at hydrogenation temperatures of below 120° C., whereas the reaction has to be carried out at hot spot temperatures as high as 150° C. and above when the prior art catalysts are used. Its low tendency to form undesirable cyclic by-products is striking. For example, in the preparation of hexamethylenediamine from adiponitrile, the concentrations of 1,2-diaminocyclohexane and azacycloheptane are substantially below 0.2%, and the concentration of 2-aminomethylcyclopentylamine is less than 0.002%. Because of its hardness, the novel catalyst possesses excellent mechanical stability. This is achieved by converting it into moldings not at the stage of the iron(III) oxides but only after the reduction of these to iron metal particles and subsequent passivation. Outstanding hardness is achieved if the molded iron catalyst material is passivated and activated alternately until a hardness of from 850 to 1500 $kp/cm^2$ is reached. If moldings which have been prepared from iron(III) oxide and lubricants and subsequently reduced are used as a starting material, the indentation hardness of the moldings decreases, for example from 300 $kp/cm^2$ to 25 $kp/cm^2$, after the degree of reduction has reached 95%. In this case, the catalyst life is less than 100 days.

The catalysts according to the invention can advantageously be used for the hydrogenation of saturated and unsaturated organic nitriles to the corresponding saturated amines.

The novel catalyst is particularly useful for the preparation of alkylamines and alkylenediamines by reaction of an alkanenitrile or alkanedinitrile of 3 to 18 carbon atoms with hydrogen in the presence of ammonia. The catalysts according to the invention have become particularly important for the preparation of hexamethylenediamine by reaction of adiponitrile with hydrogen in the presence of ammonia. In this procedure, the temperature is kept at from 80° to 140° C., preferably from 110° to 120° C., and the pressure at from 100 to 400, preferably from 200 to 300, bar. The hydrogenation is advantageously carried out in the presence of ammonia; some of this can be replaced by a recycled crude hydrogenation mixture which essentially consists of hexamethylenediamine and ammonia. It has proven useful if the volume ratio of adiponitrile to ammonia is from 1:2 to 1:20, preferably from 1:6 to 1:12.

The Examples which follow, illustrate the invention.

EXAMPLE 1

Preparation of the catalyst 600 kg of acicular lepidocrocite (δ-FeOOH) which is prepared as described in German Published Application DAS No. 1,061,760 and has a chlorine content of <0.1% and an $Na_2O$ content of <0.1%, a specific surface area of 32 $m^2/g$, a mean needle length of 0.8 μm, a length-to-width ratio of the needles of 22:1, a bulk density of 0.37 $g/cm^3$ and a pH value of 7.2 are reduced in an agitated fixed bed, at 400° C., for 38 hours, with 400 $m^3$ (S.T.P.)/h of hydrogen to give metallic iron (Fe>95%; stoichiometric excess of hydrogen: 64). The pyrophoric acicular metal pigment is then coated with a stabilizing oxide layer in a nitrogen/air mixture at 60° C., and the degree of reduction should not fall below 90%. The yield is 400 kg. The saturation magnetization of the iron particles is 153 nT $m^3/g$ in a magnetic field of 160 kA/m. The iron particles have a BET specific surface area of 7.2 $m^2/g$, and electron micrographs show that they have an anisotropic geometrical shape (acicular shape).

To produce molded materials having a diameter of 5 mm and a height of 4 mm, the stabilized pulverulent metal pigment is mixed with 2% by weight of gaphite, and the mixture is tableted under a nitrogen atmosphere. The indentation hardness of the tablets should not be less than 300 $kp/cm^2$.

EXAMPLE 2

Activation and compaction of the catalyst 350 l of the moldings (tablets) produced as described in Example 1 are introduced into a reactor having a length of 1800 mm and an internal diameter of 160 mm, and are treated with a large excess of hydrogen (64-fold) at 360° C. and 150 bar for 24 hours in order to eliminate the passivation. The hydrogen is circulated via a condenser in order to separate off the water of reduction. The degree of reduction is >98%.

Under these activation conditions, the indentation hardness of the catalyst tablets increases from 300 to 800–900 kp/cm².

When the catalyst has cooled, the hydrogen is displaced by nitrogen. The catalyst is passivated once again, using a nitrogen/air mixture containing no more than 0.5 vol.% of oxygen, the amount of gas being adjusted so that the catalyst temperature does not exceed 100° C. and the degree of reduction of the catalyst does not fall below 90%. The catalyst is then once again activated with $H_2$ under the above conditions, the indentation hardness of the tablets increasing further to 1000–1200 kp/cm². The degree of reduction is >98%.

By repeating the passivation and reduction, the indentation hardness can finally be increased to as far as 1500 kp/cm².

EXAMPLE 3

Hydrogenation of adipodinitrile

Using a trickle-bed procedure, 85 l/hour of adipodinitrile and 510 l/hour of liquid ammonia are fed into the reactor described under Example 2, which contains 350 l of the catalyst prepared as described in Example 1 and compacted and activated as described in Example 2, the hydrogen pressure being 270 bar and recycled gas being fed in at a rate of 400 m³ (S.T.P.)/h. The temperature of the feed mixture is 78° C. and the reactor exit is at 110° C.; the maximum temperature ($T_{max}$) of the temperature profile is 119° C.

Analysis of the crude hexamethylenediamine by gas chromatography after vaporization of the ammonia from the hydrogenation mixture indicates the presence of 0.02% by weight of hexylamine, 0.09% by weight of azacycloheptane, 0.11% by weight of 1,2-diaminocyclohexane and 99.78% by weight of hexamethylenediamine, and an aminocapronitrile content of ≦0.01%. The distillation residue, which consists predominantly of bis-hexamethylenetriamine, amounts to 0.36%. The selectivity with respect to hexamethylenediamine is calculated at 99.4%. The activity and selectivity of the catalyst were unchanged after a time-on-stream of 700 days without any regeneration.

The disintegration rate of the catalyst is less than 0.5%. The disintegration rate is the amount of catalyst which passes through a screen having a mesh size of 3 mm.

COMPARATIVE EXAMPLE

2% of graphite is added to δ-FeOOH, and the mixture is pressed to give tablets having a diameter of 5 mm and a height of 4 mm. The indentation hardness is brought to 300 kp/cm². The tablets are then brought to a degree of reduction of ≧95% with hydrogen at 360° C. As a result of the reduction of the δ-FeOOH, the indentation hardness of the tablets drops sharply to ≦25 kp/cm². Contact with the cylindrical surface readily results in the tablets disintegrating into disks.

In contrast to tablets produced from δ-FeOOH which has already been reduced, the mechanical stability of these tablets cannot be improved by repeated passivation and reduction.

We claim:

1. A molded iron catalyst material having an indentation hardness of from 850 to 1500 kp/cm² and containing metallic iron particles, obtained from ion oxide particles by contact with hydrogen at ≦500° C., and a lubricant.

2. A catalyst material as defined in claim 1, containing from 1 to 5% by weight of a lubricant.

3. A catalyst material as defined in claim 1, containing graphite as a lubricant.

4. A catalyst material as defined in claim 1, wherein the starting material used is anisometric gamma-iron-(III) oxide hydroxide.

5. A process for the preparation of a molded iron catalyst material containing metallic iron particles and a lubricant, by:
   (a) reduction of iron oxide particles with hydrogen at from 250° to 500° C. to metallic iron particles,
   (b) passivation of the iron particles by treatment with an inert gas containing molecular oxygen,
   (c) pressing of the passivated iron particles with a lubricant to give moldings, and
   (d) activation of the moldings by treatment with hydrogen at from 250° to 500° C., wherein the activated moldings are passivated by treatment with an inert gas containing molecular oxygen and subsequently activated by treatment with hydrogen at from 250° to 500° C., these steps being carried out once or several times.

6. The process of claim 5, wherein the passivation and activation of the moldings are carried out from once to 5 times.

7. The process of claim 5, wherein the anisometric iron oxide particles are reduced until the degree of reduction is >95%.

8. The process of claim 5, wherein, in the passivation by treatment with an inert gas containing molecular oxygen, the degree of reduction does not fall below 80%.

* * * * *

UNITED STATES PATENT AND TRADEMARK OFFICE
CERTIFICATE OF CORRECTION

PATENT NO. : 4,587,228

DATED : May 6, 1986

INVENTOR(S) : Gerhard FRANK et al.

It is certified that error appears in the above-identified patent and that said Letters Patent is hereby corrected as shown below:

IN THE CLAIMS:

Claim 1, column 6, line 14, change "ion" to --iron--.

Signed and Sealed this

Twenty-ninth Day of July 1986

[SEAL]

Attest:

Attesting Officer

DONALD J. QUIGG

Commissioner of Patents and Trademarks